(12) United States Patent
Yang

(10) Patent No.: US 7,564,361 B2
(45) Date of Patent: Jul. 21, 2009

(54) STRUCTURAL IMPROVEMENT FOR ALERT SYSTEM

(76) Inventor: Chang-Ming Yang, No. 27, Guangfu Rd., Junan Jen, Miaoli (TW)

( * ) Notice: Subject to any disclaimer, the term of this patent is extended or adjusted under 35 U.S.C. 154(b) by 181 days.

(21) Appl. No.: 10/623,450

(22) Filed: Jul. 21, 2003

(65) Prior Publication Data

US 2005/0017868 A1    Jan. 27, 2005

(51) Int. Cl.
*G08B 23/00* (2006.01)
(52) U.S. Cl. .................................................. 340/573.1
(58) Field of Classification Search .............. 340/573.1, 340/500, 540, 815.4, 384.1
See application file for complete search history.

(56) References Cited

U.S. PATENT DOCUMENTS

| | | | | |
|---|---|---|---|---|
| 5,122,091 A | * | 6/1992 | Townsend | .................... 452/127 |
| 5,198,702 A | * | 3/1993 | McCullough et al. | ....... 307/326 |
| 5,201,684 A | * | 4/1993 | DeBois, III | .................. 452/127 |
| 5,272,946 A | * | 12/1993 | McCullough et al. | .......... 83/58 |
| 5,510,685 A | * | 4/1996 | Grasselli | ..................... 318/434 |
| 6,772,939 B1 | * | 8/2004 | Simpson | ....................... 232/38 |
| 2004/0194594 A1 | * | 10/2004 | Dils et al. | ....................... 83/13 |
| 2007/0240786 A1 | * | 10/2007 | Gass et al. | .................. 144/420 |

* cited by examiner

*Primary Examiner*—Phung Nguyen
(74) *Attorney, Agent, or Firm*—Pai Patent & Trademark Law Firm; Chao-Chang David Pai; Jeffrey R. Ouimet

(57) ABSTRACT

The present invention relates to an alert system with a sensor to detect article made of metal or magnetic. When detecting any dangerous article made of metal or magnetic nearby, the sensor sends out a signal to the control panel, prompting the warning system to send out a signal or sounds to warn the user, so as to protect the user from being hurt by dangerous article made of metal or magnetic.

25 Claims, 8 Drawing Sheets

STRUCTURAL IMPROVEMENT FOR ALERT SYSTEM

BACKGROUND OF THE INVENTION

1. Field of the Invention

The present invention relates to an alert system with a sensor to detect article made of metal or magnetic and then sends the detected result to the micro-processor or the control panel to make comparison between the detected result and database. When any dangerous article made of metal or magnetic touching against the sensor, the micro-processor sends out a signal to the control panel, prompting the warning system to warn the user with signals or sounds. Meanwhile, the control panel also starts up the protection device to protect the user from being hurt by dangerous article made of metal or magnetic.

2. Description of the Prior Art

Today's medical operation still uses traditional operating tools; however, the operating knife is too sharp and the gloves too thin that make doctors fail to find any fracture or damage in the tools. Therefore, the doctors might touch the patients' blood directly because of a single hole pierced by the metal, leading to bacterial infection or disease infection and thus threatening the doctors' and the nursing staff's life.

Furthermore, cleaners cleaning up the garbage may not know the existence of dangerous article that might hurt people, such as needle head, sharp article made of metal or magnetic.

In view of such disadvantages, the inventor of the present invention was devoted to finding a solution and accomplished structural improvement for alert system.

SUMMARY OF THE INVENTION

The main objective for the present invention is to provide an alert system with a sensor called CCD able to detect article made of metal or magnetic and sends the detected result to the micro-processor, where the detected result is compared with the data in the database. If the detected result indicates the existence of article made of metal or magnetic, the micro-processor then sends out a signal to the control panel, where the warning device warns the user with sounds or signals and the protection device protects the user from being hurt.

Another objective for the present invention is to provide an alert system whose sensor can be a magnetic wave sensor that uses magnetic wave to detect article made of metal or magnetic and then sends out signals to the control panel. The control panel that detects the existence of article made of metal or magnetic sends out a signal to the warning device which warns the user with sounds or signals and protects the user from being hurt by dangerous article made of metal or magnetic.

Still another objective for the present invention is to provide an alert system whose sensor can be a thermal sensor or CCD that utilizes a thermal sensing device to detect the temperature and sends the detected results to the micro-processor. This micro-processor that receives the information from the thermal sensor and the CCD image device compares the result with the database to judge the existence of article made of metal or magnetic. If any article made of metal or magnetic is detected, the micro-processor sends out a signal the control panel, where the warning device warns the user with sounds or signals and the protection device protects the user from being hurt.

One another objective for the present invention is to provide an alert system whose sensor can be made of conductive material. When any article made of metal or magnetic touches against the conductive material, the sensor sends out a signal to the control panel where the warning device warns the user with sounds or signals. The protection device can be an airtight chamber or contains identifiable or medicinal liquid.

Still one another objective for the present invention is to provide an alert system whose sensor can be a thermal sensor or CCD that utilizes a thermal sensing device to detect the temperature of the article made of metal or magnetic. The detected results and the image information obtained by the CCD image device are converted into signals which are then delivered to the micro-processor. The micro-processor compares the image information with the database to judge the existence of article made of metal or magnetic by data of the pre-determined shape of the article made of metal or magnetic. The micro-processor that detects any article made of metal or magnetic sends out a signal to the warning device and the motor, where the warning device warns the user with sounds or signals and the motor enables the protection device to protect the user.

One more objective for the present invention is to provide an alert system whose sensor can be a diode or beeper. When the micro-processor sends out a signal to the warning device, the diode or beeper of the warning device warns the user against the article made of metal or magnetic nearby by glittering or beeping.

Also another objective for the present invention is to provide an alert system whose sensor can be an airtight chamber. When the micro-processor sends out a signal to the motor, the motor starts automatically and with air injected to the airtight chamber of the protection device which then inflates to protect the user from being hurt by article made of metal or magnetic.

The last objective for the present invention is to provide an alert system whose sensor contains identifiable liquid or medicinal liquid. When the micro-processor sends out a signal to the motor, the motor starts automatically and pressurizes the protection device to push the liquid out, thus warns the user against the article made of metal or magnetic.

The present invention relates to an alert system with a sensor designed to detect article made of metal or magnetic and then sends the detected result to the micro-processor to make comparison between the result and the database. When the sensor detects article made of metal or magnetic, the micro-processor sends out a signal to the control panel, prompting the warning system to warn the user with sounds or signals. The motor receiving the signal from the micro-processor enables the protection device to protect the user from being hurt by dangerous article made of metal or magnetic. The sensor can be a CCD image device, a thermal sensor, a conductive sensor or an electromagnetic wave sensor that sends out a signal to the micro-processor. The warning device can be a diode or a beeper that warns the user against article made of metal or magnetic by glittering or beeping after receiving the signal from the micro-processor. The protection device can be an airtight chamber or contains identifiable or medicinal liquid. The motor that receives the signal from the micro-processor pressurizes the protection device to push the liquid within, thus warns the user against the article made of metal or magnetic.

BRIEF DESCRIPTION OF THE DRAWINGS

The drawings disclose an illustrative embodiment of the present invention which serves to exemplify the various advantages and objects hereof, and are as follows.

In the following, the embodiment illustrated is used to describe the detailed structural characteristics and operation action for the present invention.

DETAILED DESCRIPTION OF THE PREFERRED EMBODIMENT

Figure 1:
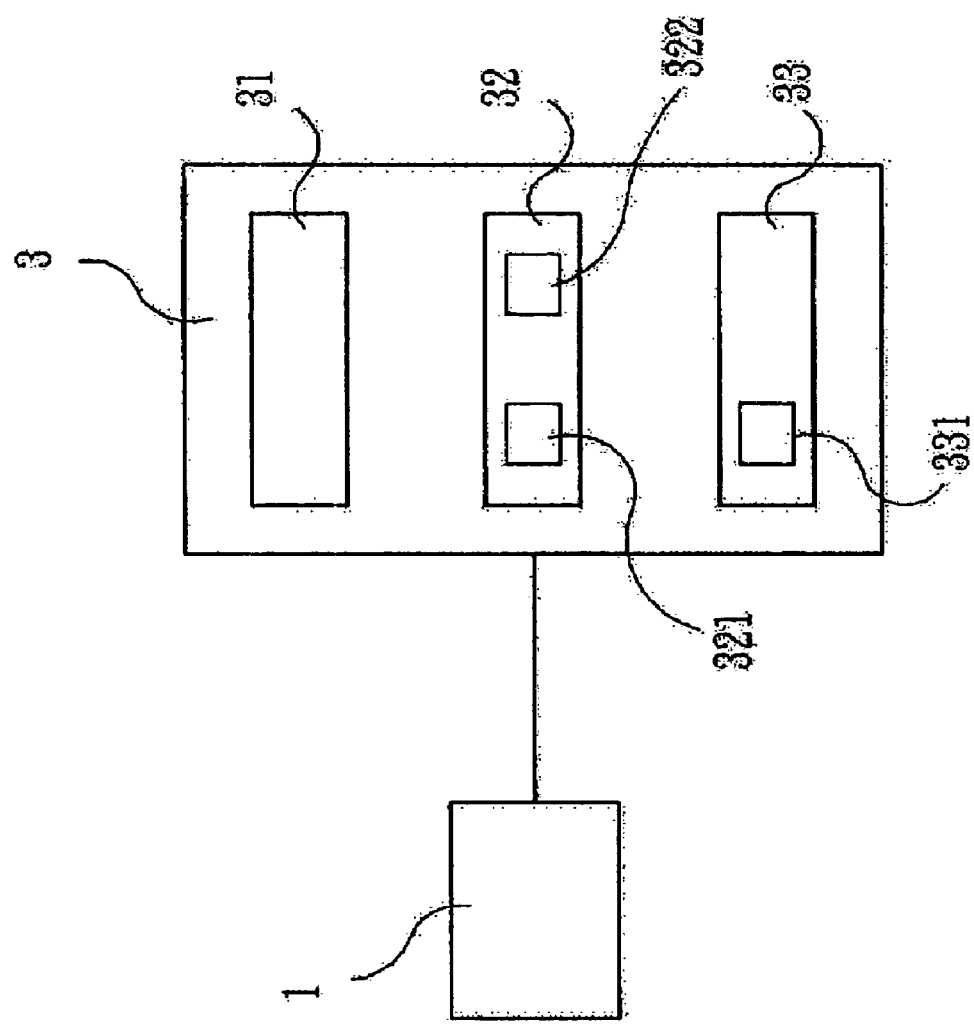
FIG. 1 is an illustration for the first type of structure for the present Invention.

Please refer to FIG. 1. The present invention contains:

a sensor 1 that sends out a signal to the control panel 3. The sensor can be made of conductive material 11, a CCD image device 14, an electromagnetic wave sensor 12, a pressure sensor 13 or a thermal sensor 15;

a control panel 3 that consists of an electronic circuit 31, a warning device 32 and a protection device 33. The control panel receives the signal from the sensor 1 to warn the user;

when article made of metal or magnetic 8 touches against the conductive material 11 of the sensor 1, putting through the electronic circuit 31 of the control panel 3, the warning device 32 is prompted to warns the user with sounds or signals. Meanwhile, the protection device 33 of the control panel 3 protects the user from being hurt by the article made of metal or magnetic. The protection device 33 could be an airtight chamber 331 (such as gas with certain smell or color) or combined with a motor 332 for pressurization. With the protection device 33 is filled with certain liquid 333 (such as colored liquid, colloid liquid) or medicinal liquid 334 the electronic circuit 31 of control panel 3 being put through starts the motor 332, pushing the liquid 333 or the medicinal liquid 334 out of the protection device 33, enabling the user to identify the liquid, and thus protect the user from being hurt. The medicinal liquid 334 could provide disinfection function when the user is wounded. The warning device 32 of the control panel 3 could be a diode 321 or a beeper 322.

In the case where the sensor 1 is a pressure sensor 13, any article made of metal or magnetic 8 that touches against the pressure sensor 13 would cause unusual pressure. Therefore, the sensor 1 sends out a signal to the electronic circuit 31 of the control panel 3 and prompts the warning device 32 to warn the user with sounds or signals. The protection device 33 of the control panel 3 consists of an airtight chamber 331 and a motor 332. When the control panel 3 receives the protection device, injecting air into the airtight chamber 331 and protects the user from being hurt by the article made of metal or magnetic. The gas inside the airtight chamber 331 of the protection device 33 can be replaced with identifiable liquid 333 (such as color liquid or colloid liquid) or medicinal liquid 334. When the electronic circuit 31 of the control panel 3 is put through which starts the motor 323 of the protection device 33, the identifiable liquid 333 and the medicinal liquid 334 would flush out from the protection device 33, warning the user against any dangerous article. The medicinal liquid 334 could provide disinfection function for the user being wounded. The warning device 32 of the control panel 3 could be a diode 321 or a beeper 322.

Figure 2:
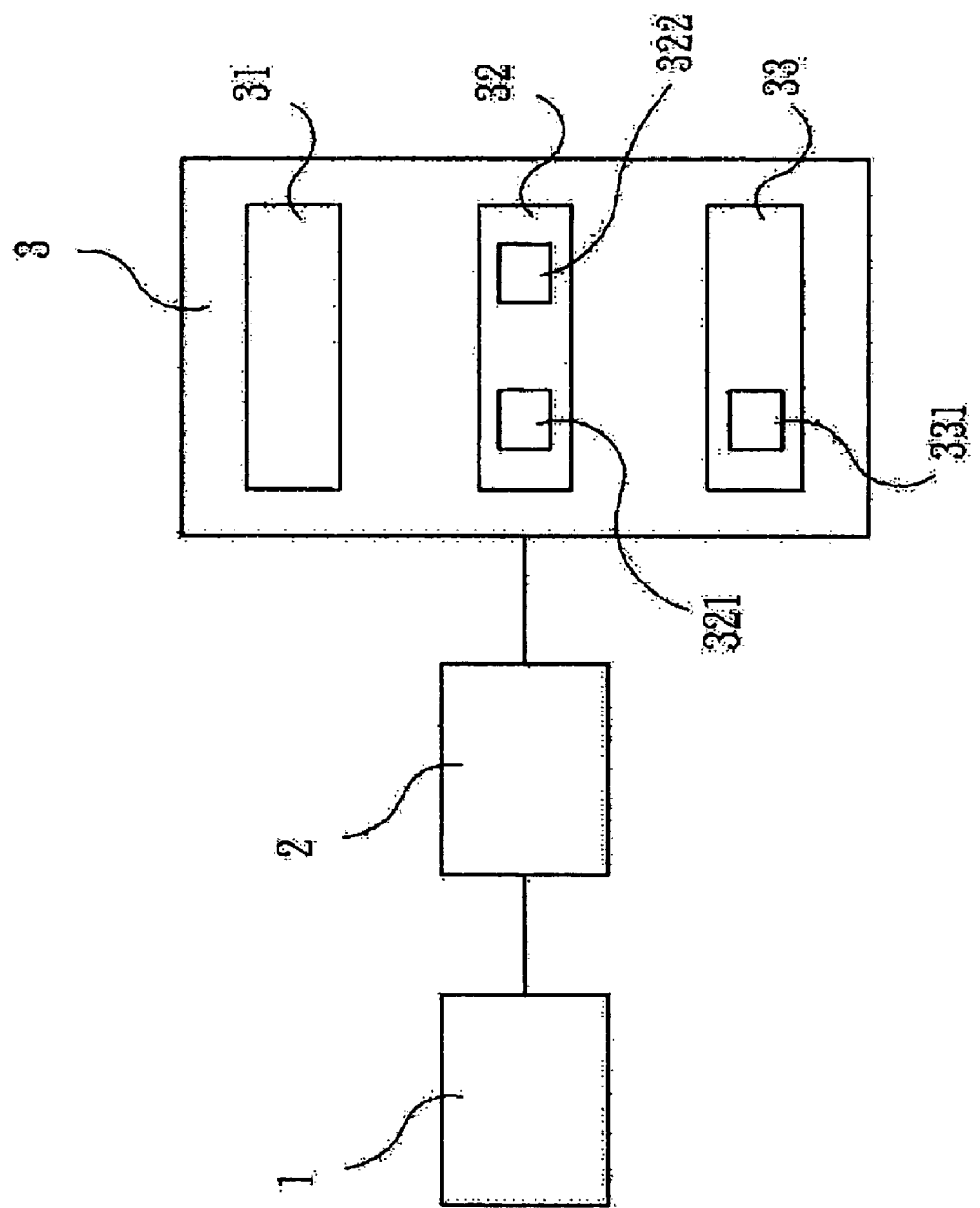
FIG. 2 is an illustration for the second type of structure for the present Invention.

Please refer to FIG. 2. The present invention contains:

a sensor 1 that sends out a signal to the micro-processor 2. The sensor can be made of conductive material 11, an electromagnetic wave sensor 12, a pressure sensor 13 or a CCD image device 14;

a micro-processor 2 that receives the signal from the sensor 1, compares the results with the database of the micro-processor 2 to judge the existence of article made of metal or magnetic 8 and thereafter sends out a signal to the control panel 3.

a control panel 3 that consists of an electronic circuit 31, a warning device 32 and a protection device 33. The control panel receives the signal from the sensor 1 to warn the user.

The present invention uses a sensor 1 to detect article made of metal or magnetic 8 and then sends the detected results to the micro-processor 2 where the results are compared with the database's information to determine whether the detected articles are made of metal or magnetic material. When detecting any article made of metal or magnetic, the micro-processor 2 sends out a signal to the control panel 3 where the warning device 31 issues a signal or sounds to warn the user and the protection device 32 of the control panel 3 protects the user from being hurt by article made of metal or magnetic 8. The sensor 1 could be a CCD image device that delivers the information obtained to the micro-processor 2 where a comparison between the result and the database is made. If the comparison result indicates the existence of article made of metal or magnetic by the pre-determined shape of the article made of metal or magnetic, the micro-processor 2 then sends out a signal to the control panel 3 where the warning device 31 issues sounds and signals to warn the user. The warning device 31 might be a diode 321 or a beeper 322. The electronic circuit 31 of the control panel 3 forces the motor 332 of the protection device 33 to inject gas into the airtight chamber 331 (such as gas with certain smell or color) to protect the user. The gas can be replaced with identifiable liquid 333 (such as colored liquid or colloid liquid) or medicinal liquid 334. The electronic circuit 31 of the control panel 3 being put through drives the motor 332 and forces the identifiable liquid 333 or the medicinal liquid 334 out of the protection device 33, so as to warn and protect the user with the identifiable liquid. The medicinal liquid 334 could provide disinfection function for the user being wounded.

The sensor 1 can contain both a thermal sensor 15 and a CCD image device 14. The temperature information obtained by the thermal sensor and the image information obtained by the CCD image device is sent to the micro-processor 2 where a comparison between the result and the database is made to see if any article made of metal or magnetic exists. When detecting any article made of metal or magnetic, the micro-processor 2 sends out a signal to the control panel where the warning device 32 warns the user with sounds or signals. The warning device 32 might be a diode 321 or a beeper 322. The electronic circuit 31 of the control panel 3 being put through drives the motor 332 of the protection device 33 to inject gas into the airtight chamber 331 (such as gas with certain smell or color) so as to protect the user. The gas can be replaced with identifiable liquid 333 (such as colored liquid or colloid liquid) or medicinal liquid 334. When the electronic circuit 31 of control panel 3 is put through, driving the motor 332 and forcing the identifiable liquid 333 or the medicinal liquid 334 out of the protection device 33, the user identifying the liquid would be warned and thus protected. The medicinal liquid 334 could provide disinfection function for the user being wounded.

Figure 3:
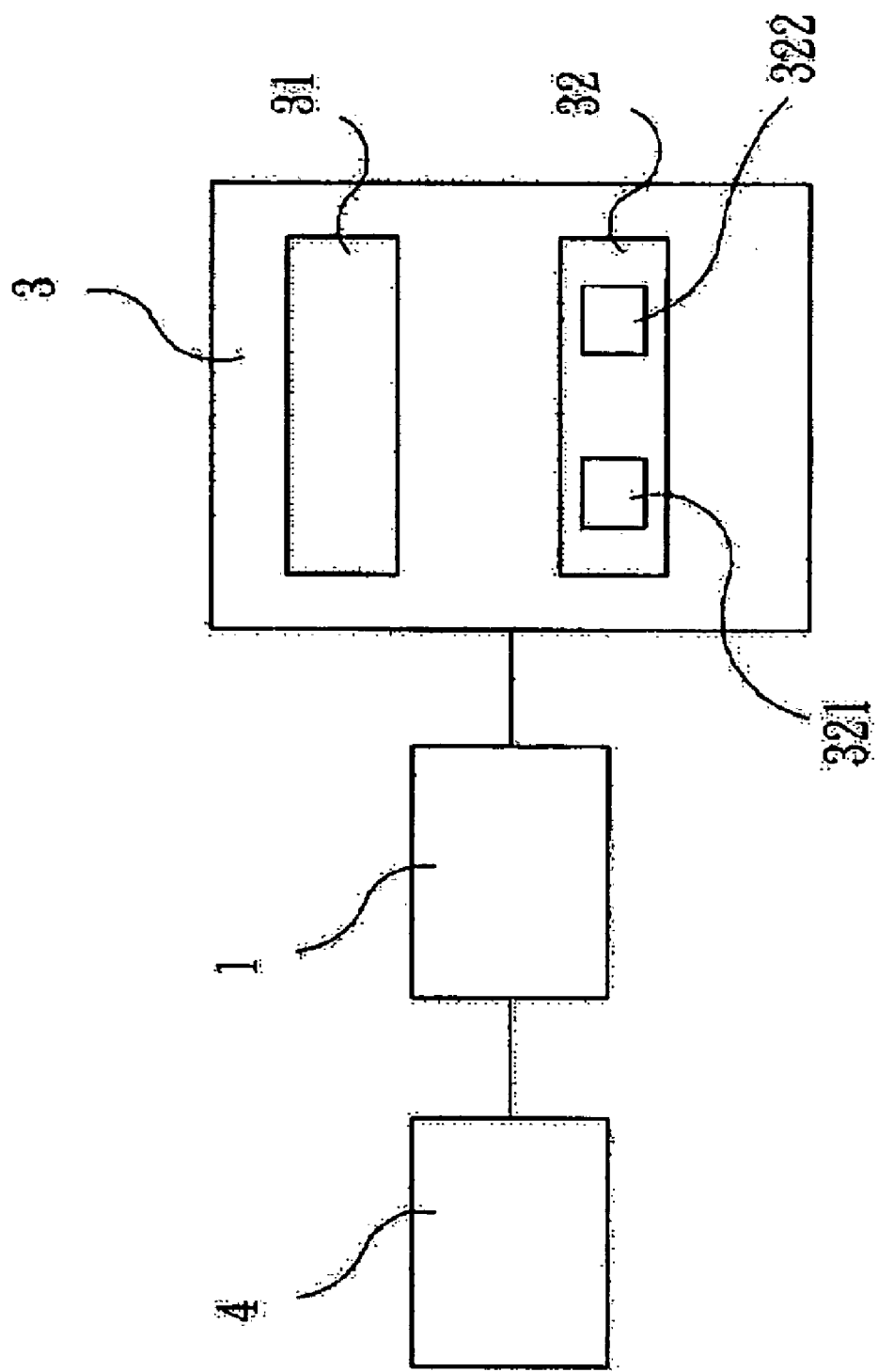
FIG. 3 is an illustration for the third type of structure for the present Invention.

Please refer to FIG. 3. The present invention contains:

a sensor 1 that sends out a signal to the control panel 3. The sensor 1 can be made of conductive material 11, an electromagnetic wave sensor 12, a pressure sensor 13 or a CCD image device 14.

a control panel 3 that receives the signal from the sensor 1 to warn the user, consisting of an electronic circuit 31, a warning device 32 and a protection device 33.

article made of metal or magnetic 8 combined with non-metal article for the convenience of the sensor's 1 detection. The non-metal article could be cotton 5, swab 6 or suture 7.

an electromagnetic wave-proof device 4 used to isolate the detection of the sensor 1. The present invention uses a sensor to detect article made of metal or magnetic 8 and then delivers the detected result to the control panel 3 where the electronic circuit 31 being put through starts the warning device 32 of the control panel 3 that receives the signal to warn the user with signals or sounds. article made of metal or magnetic 8 is placed inside the electromagnetic wave-proof device 4 to isolate the detection of the sensor 1.

The sensor 1 might be an electromagnetic wave device 12 that delivers the detected result to the control panel 3 when detecting any article made of metal or magnetic. The electronic circuit 31 being put through prompts the warning device 32 of the control panel 3 to warn the user with signals or sounds. article made of metal or magnetic 8 is placed inside the electromagnetic wave-proof device 4 to isolate the detection of the sensor 1. The electromagnetic wave-proof device 4 could be an isolation tub 41, a needle head cover or an operating knife protective sheath 42 capable of isolating the detection of the sensor 1.

Figure 4:
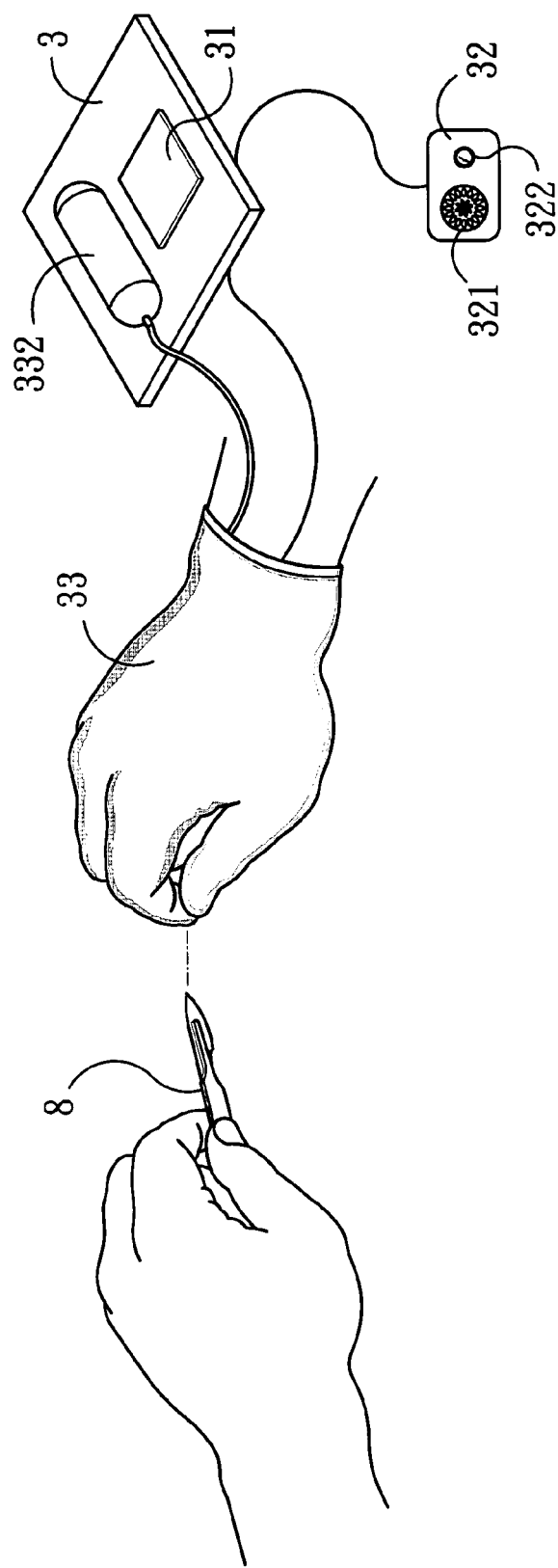
FIG. 4 is an illustration for the first type of application for the present Invention.

Please refer to FIG. 4. The sensor of the present invention is installed on a pair of multi-layer operating gloves with one layer connected to the protection device 33 of the control panel 3. The sensor is made of conductive material 11 that puts through the electronic circuit 31 of the control panel when touching against any article made of metal or magnetic 8. The electronic circuit 31 being put through starts the warning device 32 of the control panel to warn the user with sounds or signals. The protection device 33 can be an airtight chamber 331 (such as gas with certain smell or color) or combined with a motor 332 for pressurization. The protection device 33 is filled with identifiable liquid 333 (such as colored liquid, colloid liquid) or medicinal liquid 334. The electronic circuit 31 of the control panel 3 being put through drives the motor 332 that pressurizes the identifiable liquid 333 or the medicinal liquid 334 out of the protection device 33, keeping the user alerted with the liquid. The medicinal liquid 334 could provide disinfection function for the user being wounded. The warning device 32 of the control panel 3 could be a diode 321 or a beeper 322.

Figure 5:
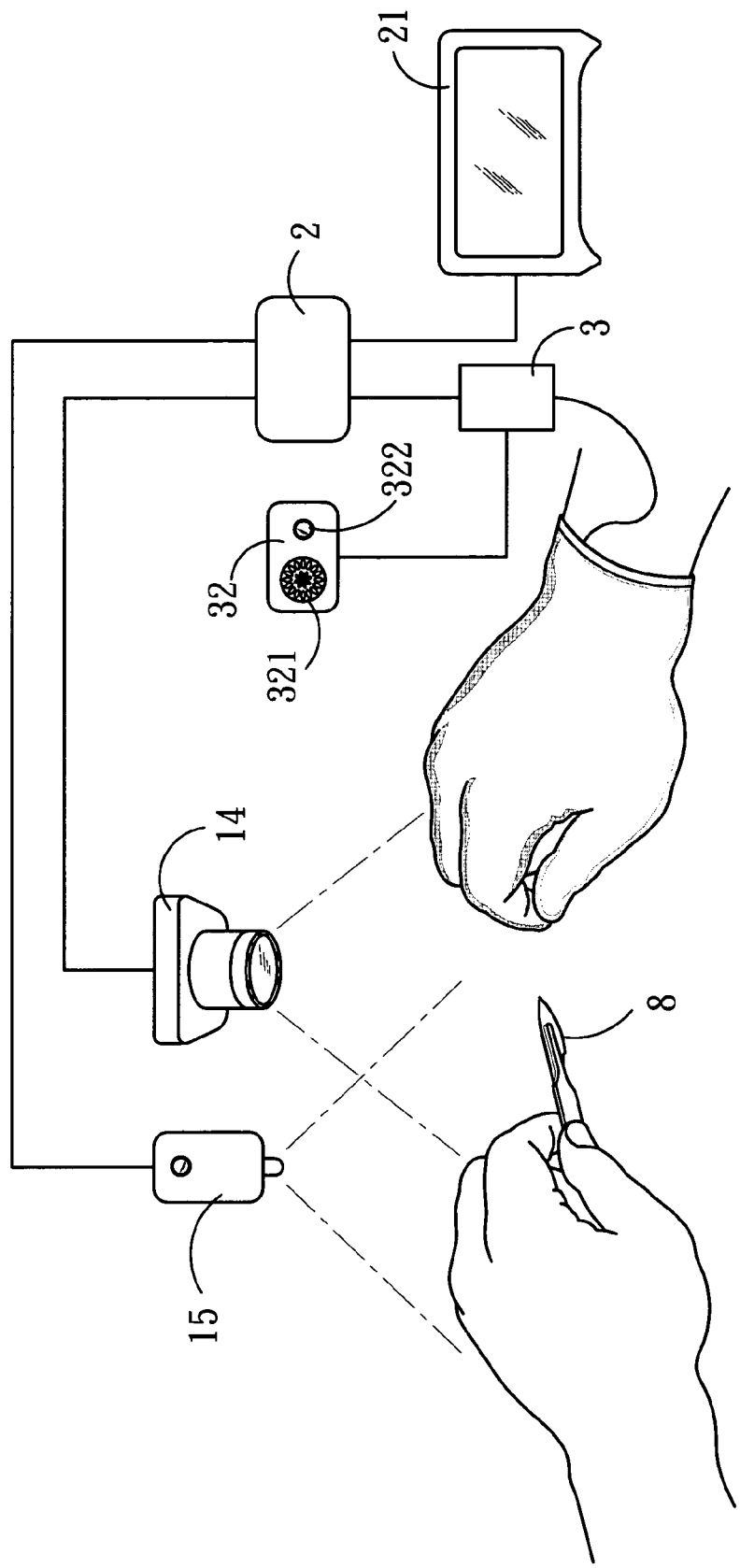
FIG. 5 is an illustration for the second type of application for the present Invention.

Please refer to FIG. 5. The sensor 1 contains both a thermal sensor 15 and CCD image device 14. The image information obtained by the CCD image device 14 and the temperature information detected by the thermal sensor 15 is delivered to the micro-processor 2 where the temperature information and image data is compared with the information in the database to judge the existence of article made of metal or magnetic 8 around. If the comparison result proves the existence of article made of metal or magnetic, a signal is delivered to the control panel 3 where the warning device 32 warns the user by sounds or signals.

Figure 6:
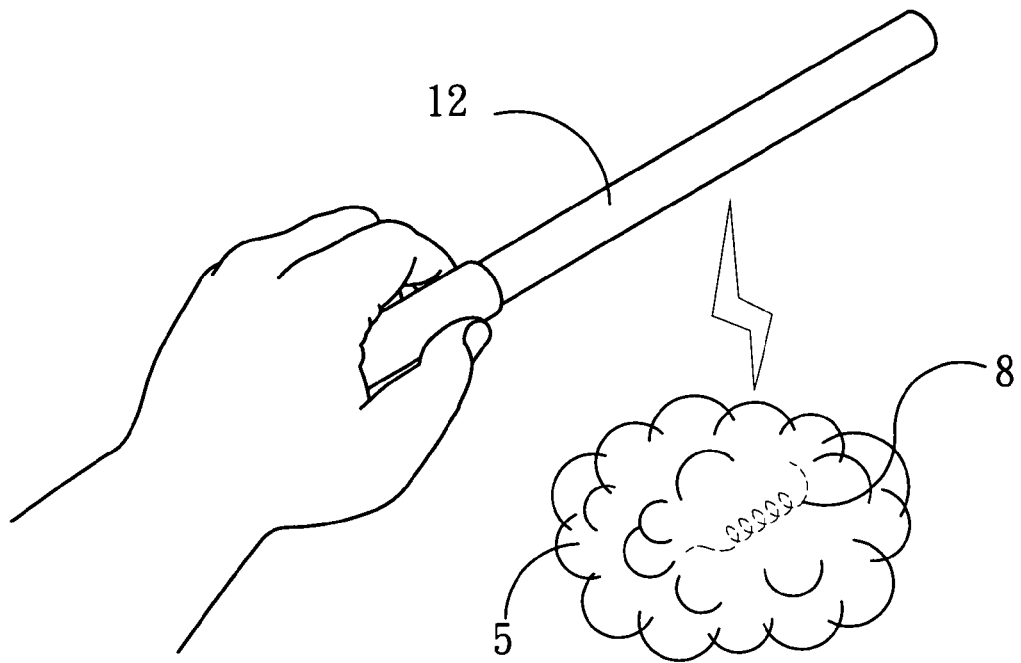
FIG. 6 and FIG. 6A illustrate the first type of application for the present invention, wherein the sensor is an electromagnetic wave sensor.
Figure 6A:
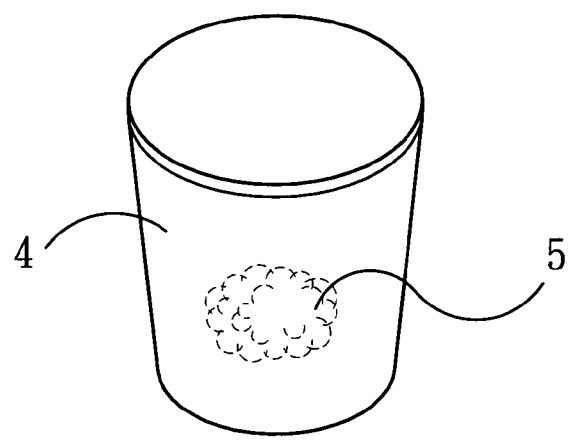

Please refer to FIG. 6 and FIG. 6A. The sensor 1 contains an electromagnetic wave sensor 12 to detect article made of metal or magnetic 8. The sensor combines article made of metal or magnetic with non-metal article so as to detect both articles. The electromagnetic wave sensor 12 detecting article made of metal or magnetic 8 sends out a signal to the control panel 3 where the warning device 32 warns the user with signals or sounds. article made of metal or magnetic is placed in an electromagnetic wave-proof device 4 designed to isolate the detection of the sensor 1. The combination of article made of metal or magnetic and non-metal article makes the detection of the electromagnetic wave sensor 12 even more convenient. The non-metal article could be cotton 5, swab 6 or suture 7.

Figure 7:
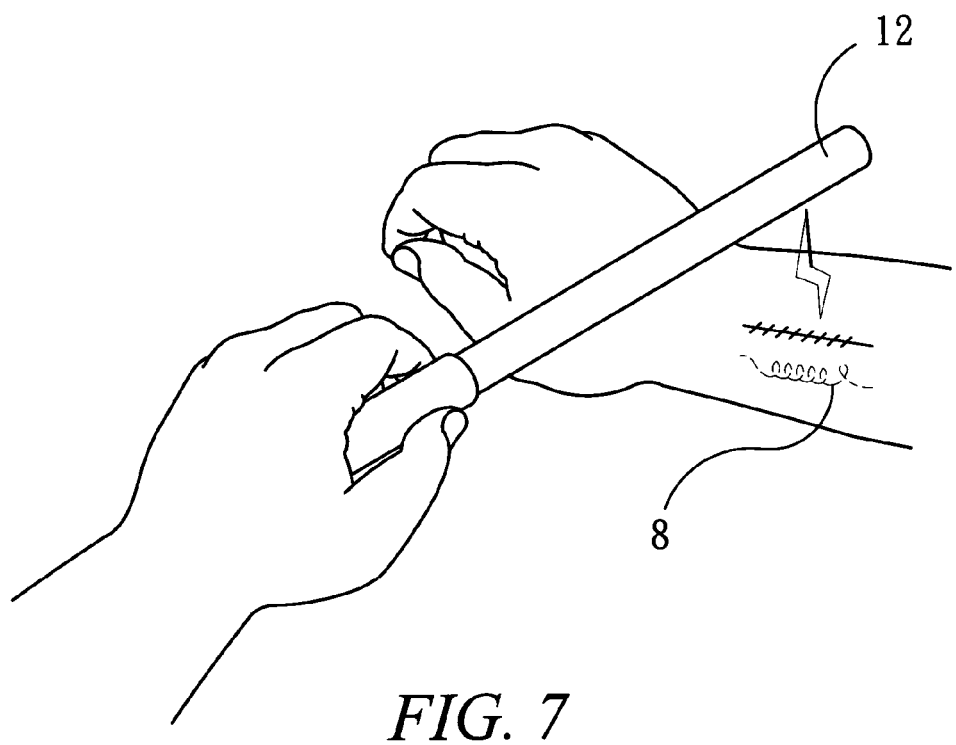
FIG. 7 is an illustration for the second type of application for the present invention, wherein the sensor is an electromagnetic wave sensor.
Figure 8:
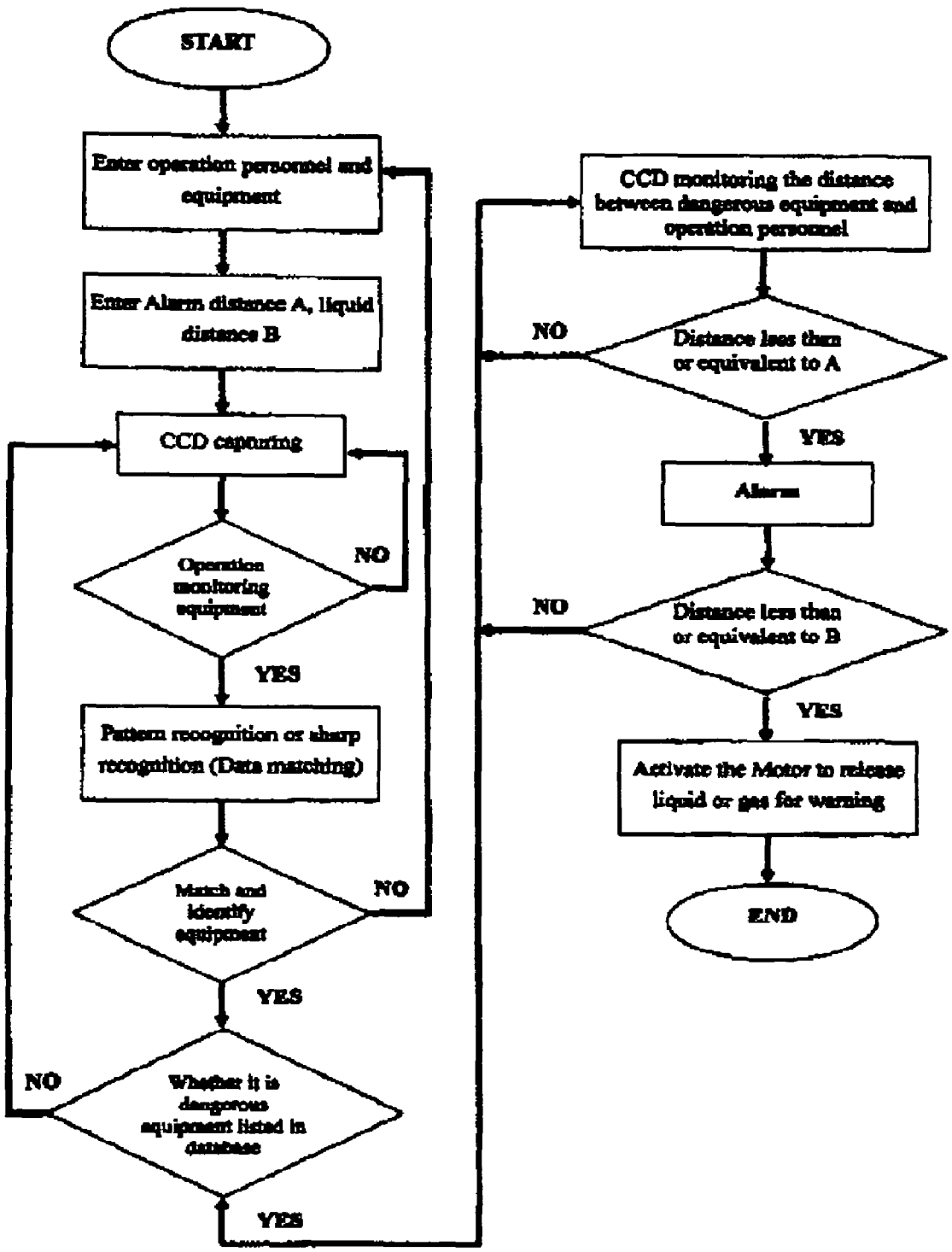
FIG. 8 is a flowchart illustrating the operation of the alert system according to the present application.

Please refer to FIG. 7. Upon the completion of the surgery, the sensor 1 with an electromagnetic wave sensor 12 can detect article made of metal or magnetic 8. With the combination of article made of metal or magnetic 8 and non-metal article, the sensor 1 is capable of detecting both kinds of article. The sensor 1 that detects article made of metal or magnetic sends out a signal to the control panel 3 to indicate the existence of article made of metal or magnetic 8. The electronic circuit 31 of the control panel 3 that receives the signal forces the warning device 32 to warn the doctor with signal or sounds that there is article made of metal or magnetic 8 inside the patient's body, thus prevents the patient's wound from inflammation and infection. The non-metal article could be cotton 5, swab 6 or suture 7.

The sensor 1 could be equipped with a capacitance sensor that shows capacitance values varying with respect to the distance between the article made of metal or magnetic and the sensor. When the capacitance value exceeds the pre-determined value, the sensor 1 sends out a signal to the electronic circuit 31 of the control panel 3, prompting the warning device 32 to warn the user with sounds or signals. The protection device 33 of the control panel 3 consists of an airtight chamber 331 and a motor 332. When the control panel 3 receives the signal from the sensor 1, the electronic circuit 31 being put through starts the motor 332 of the protection device, injecting air into the airtight chamber 331 to protects the user from being hurt by the article made of metal or magnetic. The gas inside the airtight chamber 331 of the protection device 33 can be replaced with identifiable liquid 333 (such as color liquid or colloid liquid) or medicinal liquid 334. The electronic circuit 31 of the control panel 3 being put through drives the motor 323 of the protection device 33 and pushes the identifiable liquid 333 and the medicinal liquid 334 out of the protection device 33, warning the user against dangerous article. The medicinal liquid 334 could provide disinfection function for the user being wounded. The warning device 32 of the control panel 3 could be a diode 321 or a beeper.

The present invention is to provide an alert system with the following functions:

1. The present invention uses a sensor to detect article made of metal or magnetic, wherein the sensor could be an electromagnetic wave sensor, a thermal sensor, an infrared sensor, a CCD image device or conductive material. The sensor sends the detected result to the micro-processor where the type of the material is judged. When article made of metal or magnetic is detected, the micro-processor sends a signal to the control panel where the warning device warns the user with sounds and signals and the protection device is started to protect the user from being hurt.

2. The micro-processor of the present invention that receives the signal from the sensor determines the existence of article made of metal or magnetic. When article made of metal or magnetic is detected, the micro-processor sends out a signal to the warning device and the protection device to protect the user. The micro-processor receives several signals from the sensor, compares the signals with the database to judge the existence of article made of metal or magnetic and sends out a signal to the warning device and the motor.

3. The article made of metal or magnetic of the present invention can combine with non-metal article allowing the sensor to detect article made of metal or magnetic.

4. The protection device of the present invention can contain an airtight chamber filled with liquid or medicinal liquid and a motor designed to inject air into the chamber or pressurize liquid out of the chamber to warn the user.

5. The sensor of the present invention can be equipped with a capacitance sensor that shows capacitance values varying with respect to the distance between the article made of metal or magnetic and the sensor so that location of article made of metal or magnetic can be determined.

Many changes and modifications in the above described embodiment of the invention can, of course, be carried out without departing from the scope thereof. Accordingly, to promote the progress in science and the useful arts, the invention is disclosed and is intended to be limited only by the scope of the appended claims.

What is claimed is:

1. A structural improvement for an alert system which comprises:
    a sensor installable on an operating glove and a control panel comprising an electronic circuit, a protection device and a warning device;
    wherein when a metal or magnetic material touches said sensor's conductive material, said sensor's conductive material sends a signal to said control panel that starts said control panel's warning device to warn users with a warning signal, and said control panel's protection device protects users from being hurt by said metal or magnetic material.

2. The improved alert system of claim 1, wherein said sensor is made of electroplated metal that sends out a signal to said control panel's electronic circuit when detecting any metal or magnetic material, and said control panel's electronic circuit upon receiving the signal from said sensor prompts said warning device to warn users with said warning signal and drives a motor to inject gas into said control panel's protection device designed as an airtight chamber to protect users from being hurt by said metal or magnetic material.

3. The improved alert system of claim 1, wherein said sensor is made of electroplated metal that sends out a signal to said control panel's electronic circuit when detecting any metal or magnetic material, and said control panel's electronic circuit upon receiving the signal from said sensor prompts said warning device to warn users with said warning signal and drives a motor to pressurize liquid inside said control panel's protection device out of said protection device to protect users from being hurt by said metal or magnetic material.

4. The improved alert system of claim 1, wherein said sensor is made of electroplated metal that sends out a signal to said control panel's electronic circuit when detecting any metal or magnetic material, and said control panel's electronic circuit upon receiving the signal from said sensor prompts said warning device to warn users with said warning signal and drives a motor to pressurize medicinal liquid inside said control panel's protection device out of said protection device to provide disinfection function.

5. The improved alert system of claim 1, wherein said sensor is a pressure sensor that sends out a signal to said control panel's electronic circuit when detecting any metal or magnetic material that changes pressure inside said pressure sensor, and said control panel's electronic circuit upon receiving the signal from said sensor prompts said control panel's warning device to warn users with said warning signal and drives a motor to inject gas into said control panel's protection device designed as an airtight chamber to protect users from being hurt by said metal or magnetic material.

6. The improved alert system of claim 1, wherein said sensor is a pressure sensor that sends out a signal to said control panel's electronic circuit when detecting any metal or magnetic material that changes pressure inside said pressure sensor; and said control panel's electronic circuit upon receiving the signal from said sensor prompts said control panel's warning device to warn users with said warning signal and drives a motor to pressurize liquid inside said control panel's protection device out of said protection device to protect users from being hurt by said metal or magnetic material.

7. The improved alert system of claim 1, wherein said sensor is a pressure sensor that sends out a signal to said control panel's electronic circuit when detecting any metal or magnetic material that changes pressure inside said sensor; and said control panel's electronic circuit upon receiving the signal from said sensor prompts said control panel's warning device to warn users with said warning signal and drives a motor to pressurize medicinal liquid inside said control panel's protection device out of said protection device to provide disinfection function.

8. The improved alert system of claim 1, wherein said control panel's warning device is a diode that emits light as the warning signal to warn users.

9. The improved alert system of claim 1, wherein said control panel's warning device is a beeper that produces a beeping sound to warn users.

10. A structural improvement for an alert system which comprises:
    a sensor capable of detecting a metal or magnetic material and sending out a signal to a control panel;
    a micro-processor for receiving signals from said sensor, comparing said signals with a database's data to judge the existence of metal or magnetic material, and sending out signals to said control panel;
    wherein said control panel consists of an electronic circuit, a protection device and a warning device to receive signals from said micro-processor for protection; when said metal or magnetic material approaches said sensor, said sensor sends out a signal to said micro-processor where a comparison between a detected result and said database is made; said sensor detecting any metal or magnetic material sends out a signal to said control panel which prompts said warning device to warn users with a warning signal and said protection device to protect users from being hurt by metal or magnetic material.

11. The improved alert system of claim 10, wherein said sensor contains a CCD image device that delivers image information to said micro-processor where a comparison between said image information and said database is made to judge existence of metal or magnetic material; said micro-processor detecting any metal or magnetic material then sends out a signal to said control panel, prompting said warning device to warn users with sounds or signals.

12. The improved alert system of claim 10, wherein said control panel's warning device is a diode that emits light as the warning signal to warn users.

13. The improved alert system of claim 10, wherein said control panel's warning device is a beeper that produces a beeping sound as the warning signal to warn users.

14. The improved alert system of claim 10, wherein said control panel's protection device contains an airtight chamber, a motor for gas injection and electronic circuit gas injects; said control panel receiving signals from said sensor relays the signals to said control panel's electronic circuit gas injects, driving said motor to inject gas into said airtight chamber to protect users from being hurt by metal or magnetic material.

15. The improved alert system of claim 10, wherein said control panel's protection device contains a motor and liquid; said control panel receiving signals from said sensor relays the signals to said control panel's electronic circuit, driving said motor to pressurize said liquid out of said protection device to protect users from being hurt by metal or magnetic material.

16. The improved alert system of claim 10, wherein said control panel's protection device contains a motor and medicinal liquid; said control panel receiving signals from said sensor relays the signals to said control panel's electronic circuit, driving said motor to pressurize said medicinal liquid out of said protection device to provide disinfection function.

17. A structural improvement for an alert system, which comprises:
- a sensor capable of detecting metal or magnetic material and sending out a signal to a control panel;
- said control panel that receives signals from said sensor, comprising an electronic circuit, and a warning device;
- a metal or magnetic material combined with a non-metal material for detection; and
- an electromagnetic wave-proof device for isolating said combined metal or magnetic material with non-metal material from said sensor's detection;
- wherein said sensor sends out said signal to said control panel when detecting any metal or magnetic material outside of said electromagnetic wave-proof device, and said warning device is prompted to warn users with sounds or signals that said metal or magnetic material outside of said electromagnetic wave-proof device should be placed inside said electromagnetic wave-proof device to isolate said metal or magnetic material from said sensor's further detection to prevent signal error.

18. The improved alert system of claim 17, wherein said sensor is an electromagnetic wave sensor that sends out a signal to said control panel when detecting any metal or magnetic material.

19. The improved alert system of claim 17, wherein said electromagnetic wave-proof device is an isolation tub used to isolate detection of said sensor.

20. The improved alert system of claim 17, wherein said electromagnetic wave-proof device is a needle head cover used to isolate detection of said sensor.

21. The improved alert system of claim 17, wherein said electromagnetic wave-proof device is a pair of protection gloves for operating knifes, designed for isolating said sensor's detection.

22. The improved alert system of claim 17, wherein said non-metal material is cotton.

23. The improved alert system of claim 17, wherein said non-metal material is swab.

24. The improved alert system of claim 17, wherein said non-metal material is suture.

25. The improved alert system of claim 1, 10 or 17, wherein said sensor is equipped with a capacitance sensor that shows capacitance values varying with respect to the distance between the metal or magnetic material and the sensor so that location of the metal or magnetic material is determined.

* * * * *